United States Patent
Kim et al.

(10) Patent No.: US 10,538,663 B2
(45) Date of Patent: Jan. 21, 2020

(54) PHOSPHORUS COMPOUNDS, SYNTHESIS METHOD THEREOF, AND POLYCARBONATE RESIN COMPOSITION INCLUDING THEM

(71) Applicant: RESEARCH & BUSINESS FOUNDATION SUNGKYUNKWAN UNIVERSITY, Suwon-si (KR)

(72) Inventors: Jinhwan Kim, Seoul (KR); Soo-Jung Kang, Anyang-si (KR); Vo Thi Hai, Suwon-si (KR); Sang-Won Park, Seoul (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 16/106,180

(22) Filed: Aug. 21, 2018

(65) Prior Publication Data

US 2019/0071566 A1 Mar. 7, 2019

(30) Foreign Application Priority Data

Sep. 4, 2017 (KR) .................. 10-2017-0112762

(51) Int. Cl.
| | |
|---|---|
| C08K 5/523 | (2006.01) |
| C08L 69/00 | (2006.01) |
| C08K 5/527 | (2006.01) |
| C07F 9/117 | (2006.01) |

(52) U.S. Cl.
CPC .............. C08L 69/00 (2013.01); C07F 9/117 (2013.01); C08K 5/523 (2013.01); C08K 5/527 (2013.01); C08L 2201/02 (2013.01)

(58) Field of Classification Search
CPC ......... C08K 5/523; C08K 5/527; C08L 69/00; C07F 9/117
See application file for complete search history.

(56) References Cited

FOREIGN PATENT DOCUMENTS

| | | |
|---|---|---|
| JP | 54-80355 A | 6/1979 |
| JP | 9-48972 A | 2/1997 |
| JP | 10-204276 A | 8/1998 |
| KR | 10-2007-0064924 A | 6/2007 |
| KR | 10-2015-0128569 A | 11/2015 |
| KR | 10-1738740 B1 | 5/2017 |

OTHER PUBLICATIONS

Vothi, Hai, et al., "Thermal stability and flame retardancy of novel phloroglucinol based organo phosphorus compound", *Polymer Degradation and Stability*, 2010, pp. 1092-1098, vol. 95 (7 pages in English).
Korean Office Action dated Sep. 21, 2018 in corresponding Korean Patent Application No. 10-2017-0112762 (9 pages in Korean).

*Primary Examiner* — Jeffrey H Murray
(74) *Attorney, Agent, or Firm* — NSIP Law

(57) ABSTRACT

The present disclosure relates to a phosphorus compound represented by the following Chemical Formula 1.

[Chemical Formula 1]

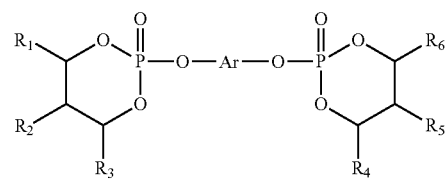

In the above Chemical Formula 1, Ar is aryl and $R_1$, $R_2$, $R_3$, $R_4$, $R_5$, and $R_6$ are each independently H, substitutable linear or branched $C_1$-$C_{20}$ alkyl and substitutable $C_6$-$C_{20}$ aryl, the aryl includes a member selected from the group consisting of phenyl, biphenyl, naphthalene, fluorene, anthracene, phenanthrene, pyrene, fluoranthen, chrysene, benzofluoranthen, perylene, quinoline, indenoanthracene, indenophenanthrene, hydroanthracene, dibenzothiophen, dibenzofuran, and combinations thereof, and the substitution is substitution with $C_1$-$C_6$ alkyl or $C_6$-$C_{20}$ aryl, but may not be limited thereto.

11 Claims, 1 Drawing Sheet

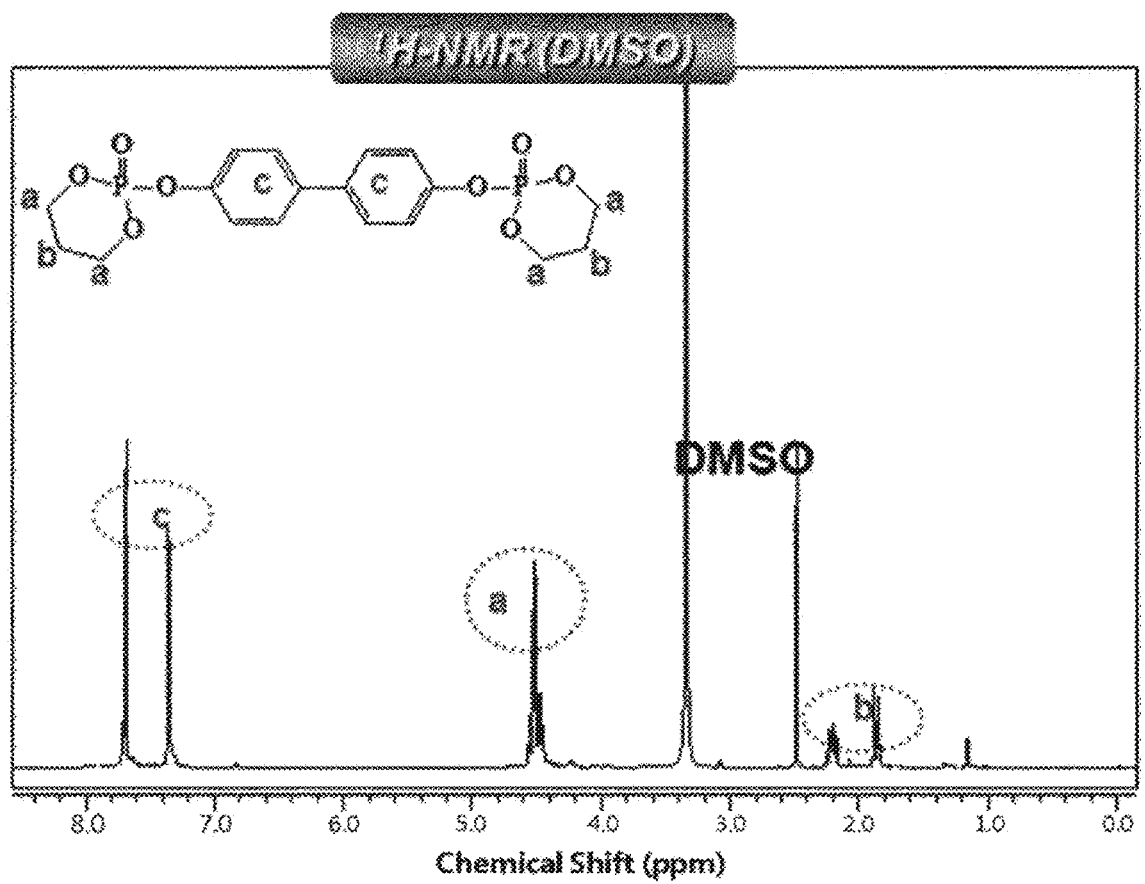

PHOSPHORUS COMPOUNDS, SYNTHESIS METHOD THEREOF, AND POLYCARBONATE RESIN COMPOSITION INCLUDING THEM

CROSS-REFERENCE TO RELATED APPLICATION

This application claims the benefit of Korean Patent Application No. 10-2017-0112762 filed on Sep. 4, 2017, the disclosure of which is incorporated herein by reference in its entirety.

TECHNICAL FIELD

The present disclosure relates to novel phosphorus compounds, a synthesis method thereof, and a polycarbonate resin composition including them.

BACKGROUND

A polycarbonate (PC) resin collectively refers to polymeric compounds having a carbonate ester structure with balanced impact strength and tensile strength and has excellent mechanical properties and a small variation in strength with temperature and thus has been widely used in various fields of machinery, electrics, components, helmets, engineering plastic, automobiles, and the like. However, PC is a thermoplastic resin without resistance to fire. Therefore, various studies have been conducted to impart flame retardancy to the PC resin.

Conventionally, a technology of mixing a halogenated flame retardant and antimony oxide has been usually used to impart flame retardancy to the PC resin. The halogenated flame retardant shows excellent flame retardancy but generates a gas adversely affecting humans and the environment during combustion. Therefore, a flame retardation technology using non-halogenated compounds is needed.

A flame retardation technology for polymer resins including inorganic compounds such as magnesium hydroxide, aluminum hydroxide, etc., as flame retardants using non-halogenated compounds has been suggested. Japanese Patent Laid-open Publication No. 10-204276 discloses a method of imparting flame retardancy to a resin by mixing aluminum hydroxide and one or more nitrogen compounds and red phosphorus and adding the mixture into an unsaturated polyester resin. However, the need for use of a large amount of aluminum hydroxide results in degradation of mechanical properties of a resin composition. Further, Korean Patent Laid-open Publication No. 2007-0064924 uses a brominated organic compound as an acrylonitrile-butadiene-styrene copolymer resin (ABS resin) which is not environment-friendly.

In general, the kind of a flame retardant to impart optimum flame retardancy varies depending on the kind of a resin. For example, if magnesium hydroxide is used as a flame retardant for an ABS resin, it cannot serve as a proper flame retardant due to chemical reaction during combustion. However, antimony oxide has been used as a retardant having the highest flame-retardant effect. Meanwhile, if magnesium hydroxide which is not proper for the ABS resin is used as a flame retardant for an acrylic resin, the highest flame-retardant effect can be obtained, and in this case, antimony oxide does not have a significant flame-retardant effect (Haekyung Park, Study on Flame Retardancy of Plastic Resin Depending on Kind of Flame Retardant, Korean Institute of Fire Science & Engineering Joint Fall Conference Proceedings 2005).

In recent years, resorcinol bis(diphenyl phosphate) (RDP), bisphenol A bis(diphenyl phosphate) (BDP), triphenyl phosphate (TPP), etc. have been widely used as phosphorous flame retardants. Particularly, RDP has low molecular weight and viscosity but has a high phosphorus (P) content, and, thus, even if a small amount of RDP is mixed in a PC resin, it is possible to obtain high flame retardancy and high fluidity. Further, the softening temperature can be reduced by about 10° C. to about 20° C., and, thus, the processing temperature can be reduced. Such a reduction in processing temperature enables the manufacturing of a high-quality product in a mold having a complicated structure and suppresses various side effects, such as mold deposition, occurring when molding is performed at a high temperature for a long time.

However, the use of a large amount of flame retardant results in degradation of optical or mechanical properties, and the use of a small amount of flame retardant makes it difficult to obtain desired flame retardancy.

Korean Patent No. 10-1738740 which is the background technology of the present disclosure relates to a halogen-free transparent flame retardant polycarbonate resin composition and a molded product. However, this prior art does not describe biphenyl cyclic 1,3-propanediol phosphate which is a novel non-halogenated flame retardant.

SUMMARY

In view of the foregoing, the present disclosure provides novel phosphorus compounds, a synthesis method thereof, and a polycarbonate resin composition including them.

However, problems to be solved by the present disclosure are not limited to the above-described problems. There may be other problems to be solved by the present disclosure.

According to a first aspect of the present disclosure, there is provided a phosphorus compound represented by the following Chemical Formula 1.

[Chemical Formula 1]

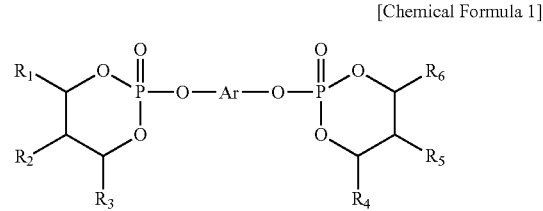

In the above Chemical Formula 1, Ar is aryl and $R_1$, $R_2$, $R_3$, $R_4$, $R_5$, and $R_6$ are each independently H, substitutable linear or branched $C_1$-$C_{20}$ alkyl and substitutable $C_6$-$C_{20}$ aryl, the aryl includes a member selected from the group consisting of phenyl, biphenyl, naphthalene, fluorene, anthracene, phenanthrene, pyrene, fluoranthen, chrysene, benzofluoranthen, perylene, quinoline, indenoanthracene, indenophenanthrene, hydroanthracene, dibenzothiophen, dibenzofuran, and combinations thereof, and the substitution is substituted with $C_1$-$C_6$ alkyl or $C_6$-$C_{20}$ aryl, but may not be limited thereto.

According to an embodiment of the present disclosure, $R_1$, $R_2$, $R_3$, $R_4$, $R_5$, and $R_6$ may be each independently H or substitutable linear or branched $C_1$-$C_{20}$ alkyl, and the substitution may be substituted with $C_1$-$C_6$ alkyl or $C_6$-$C_{20}$ aryl, but may not be limited thereto.

According to an embodiment of the present disclosure, the phosphorous compound may include the following compound, but may not be limited thereto.

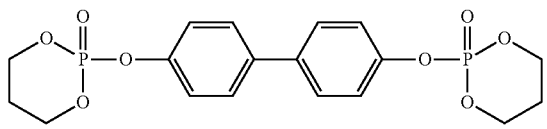 [SMILES: O=P1(Oc2ccc(-c3ccc(OP4(=O)OCCCO4)cc3)cc2)OCCCO1]

According to a second aspect of the present disclosure, there is provided a synthesis method of the phosphorous compound, including reacting a compound represented by the following Chemical Formula 2 with a compound represented by the following Chemical Formula 3.

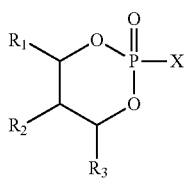

[Chemical Formula 2]

According to an embodiment of the present disclosure, in the above Chemical Formula 2, $R_1$, $R_2$, and $R_3$ are each independently H, substitutable linear or branched $C_1$-$C_{20}$ alkyl and substitutable $C_6$-$C_{20}$ aryl, the substitution is substituted with $C_1$-$C_6$ alkyl or $C_6$-$C_{20}$ aryl, and X includes one or more halogen elements selected from the group consisting of F, Cl, Br, and I, but may not be limited thereto.

 [Chemical Formula 3]

According to an embodiment of the present disclosure, in the above Chemical Formula 3, Ar is aryl, the aryl includes a member selected from the group consisting of phenyl, biphenyl, naphthalene, fluorene, anthracene, phenanthrene, pyrene, fluoranthen, chrysene, benzofluoranthen, perylene, quinoline, indenoanthracene, indenophenanthrene, hydroanthracene, dibenzothiophen, dibenzofuran, and combinations thereof, but may not be limited thereto.

According to an embodiment of the present disclosure, the aryl may be biphenyl, but may not be limited thereto.

According to a third aspect of the present disclosure, there is provided a polycarbonate resin composition including the phosphorous compound, a polycarbonate resin, and a non-halogenated flame retardant.

According to an embodiment of the present disclosure, the non-halogenated flame retardant may include a phosphate flame retardant, but may not be limited thereto.

According to an embodiment of the present disclosure, the phosphate flame retardant may be a flame retardant selected from the group consisting of resorcinol bis(diphenyl phosphate) (RDP), bisphenol A bis(diphenyl phosphate) (BDP), triphenyl phosphate (TPP), aromatic phosphate, aromatic diphosphate, aromatic triphosphate, aromatic polyphosphate, trimethyl phosphate (TMP), triethyl phosphate (TEP), tricresyl phosphate (TCP), trixylenyl phosphate (TXP), and combinations thereof, but may not be limited thereto.

According to an embodiment of the present disclosure, the polycarbonate resin composition may contain 0.1 part by weight to 50 parts by weight of the phosphorous compound and 0.1 part by weight to 50 parts by weight of the non-halogenated flame retardant relative to 100 parts by weight of the polycarbonate resin, but may not be limited thereto.

According to an embodiment of the present disclosure, the polycarbonate resin may include a compound represented by the following Chemical Formula 4, but may not be limited thereto.

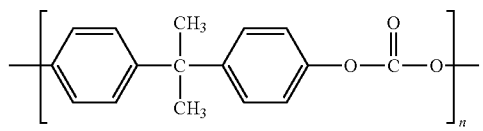

[Chemical Formula 4]

According to an embodiment of the present disclosure, in the above Chemical Formula 4, n may be 50 or more, but may not be limited thereto.

According to a fourth aspect of the present disclosure, there is provided a flame retardant molded article including the polycarbonate resin composition.

According to an embodiment of the present disclosure, the polycarbonate flame retardant resin composition may further include a material selected from the group consisting of a lubricant, an antioxidant, a photostabilizer, a chain extender, a catalyst, a release agent, a pigment, a dye, an anti-static agent, an antimicrobial agent, a processing aid, a metal deactivator, an anti-burning agent, an inorganic filler, glass fiber, an anti-friction agent, an antiwear agent, a coupling agent, and combinations thereof, but may not be limited thereto.

The above-described embodiments are provided by way of illustration only and should not be construed as liming the present disclosure. Besides the above-described embodiments, there may be additional embodiments described in the accompanying drawings and the detailed description.

According to the above-described aspects of the present disclosure, novel phosphorus compounds of the present disclosure have high flame retardancy even if they are added in a small amount onto a polymer resin such as a polycarbonate resin. Therefore, it is possible to reduce the amount of flame retardant and also possible to improve the properties of products.

The phosphorus compounds of the present disclosure can provide excellent flame retardancy when added to a polymer resin. Particularly, polycarbonate resins containing the phosphorus compounds can be applied to various industrial products requiring flame retardancy and mechanical properties.

Further, the phosphorus compounds of the present disclosure do not contain halogenated compounds and thus are environment-friendly. Furthermore, the phosphorus compounds of the present disclosure do not generate a gas harmful to humans during combustion, and, thus, the safety of those working in the relevant industries can be improved.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

FIG. 1 is a NMR (nuclear magnetic resonance) graph of BP-CPP according to an example of the present disclosure.

DETAILED DESCRIPTION

Hereinafter, embodiments of the present disclosure will be described in detail with reference to the accompanying drawings so that the present disclosure may be readily implemented by those skilled in the art.

However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the terms "on", "above", "on an upper end", "below", "under", and "on a lower end" that are used to designate a position of one element with respect to another element include both a case that the one element is adjacent to the other element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Through the whole document, the term "aryl" refers to a $C_6$-30 aromatic cyclic hydrocarbon group, for example, aromatic rings such as phenyl, naphthyl, biphenyl, terphenyl, fluorene, phenanthrenyl, triphenylenyl, pherylenyl, crysenyl, fluoranthenyl, benzofluorenyl, benzotriphenylenyl, benzocrysenyl, anthracenyl, stilbenyl, pyrenyl, and the like.

Through the whole document, the term "alkyl" may include linear or branched, saturated or unsaturated $C_1$-$C_6$ alkyl, and may include, for example, methyl, ethyl, propyl, butyl, pentyl, hexyl, or all the possible isomers thereof, but may not be limited thereto.

Through the whole document, the term "halogen" refers to an element from Group 17 of the periodic table, and may include, for example, F, Cl, Br, or I, but may not be limited thereto.

Hereinafter, novel phosphorus compounds, a synthesis method thereof, and a polycarbonate resin composition including them according to the present disclosure will be described in detail with reference to embodiments and examples and the accompanying drawings. However, the present disclosure may not be limited to the following embodiments, examples and drawings.

A first aspect of the present disclosure relates to a phosphorus compound represented by the following Chemical Formula 1.

[Chemical Formula 1]

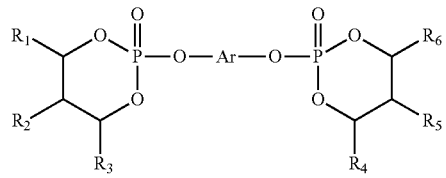

In the above Chemical Formula 1, Ar is aryl and $R_1$, $R_2$, $R_3$, $R_4$, $R_5$, and $R_6$ are each independently H, substitutable linear or branched $C_1$-$C_{20}$ alkyl and substitutable $C_6$-$C_{20}$ aryl, and the aryl includes a member selected from the group consisting of phenyl, biphenyl, naphthalene, fluorene, anthracene, phenanthrene, pyrene, fluoranthen, chrysene, benzofluoranthen, perylene, quinoline, indenoanthracene, indenophenanthrene, hydroanthracene, dibenzothiophen, dibenzofuran, and combinations thereof, and the substitution is substituted with $C_1$-$C_6$ alkyl or $C_6$-$C_{20}$ aryl, but may not be limited thereto.

According to an embodiment of the present disclosure, $R_1$, $R_2$, $R_3$, $R_4$, $R_5$, and $R_6$ may be each independently H or substitutable linear or branched $C_1$-$C_{20}$ alkyl, and the substitution may be substitution with $C_1$-$C_6$ alkyl or $C_6$-$C_{20}$ aryl, but may not be limited thereto.

According to an embodiment of the present disclosure, the phosphorous compound may include the following compound, but may not be limited thereto.

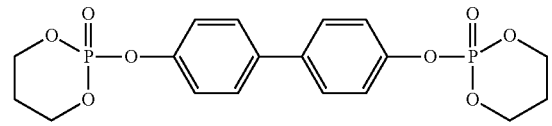

The phosphorus compound is a novel material and can provide excellent flame retardancy when added to a polymer resin. Particularly, polycarbonate resin containing the phosphorus compound can be applied to various industrial products requiring flame retardancy and mechanical properties.

Further, the phosphorus compound does not contain halogenated compounds and thus is environment-friendly. Furthermore, the phosphorus compound does not generate a gas harmful to humans during combustion, and, thus, the safety of those working in the relevant industries can be improved.

Moreover, the phosphorus compound has high flame retardancy even if it is added in a small amount onto a polymer resin such as a polycarbonate resin. Therefore, it is possible to reduce the amount of flame retardant and also possible to improve the properties of products.

A second aspect of the present disclosure relates to a synthesis method of the phosphorous compound, including reacting a compound represented by the following Chemical Formula 2 with a compound represented by the following Chemical Formula 3.

[Chemical Formula 2]

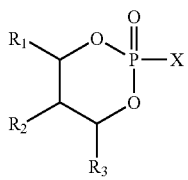

According to an embodiment of the present disclosure, in the above Chemical Formula 2, $R_1$, $R_2$, and $R_3$ are each independently H, substitutable linear or branched $C_1$-$C_{20}$ alkyl and substitutable $C_6$-$C_{20}$ aryl, the substitution is substituted with $C_1$-$C_6$ alkyl or $C_6$-$C_{20}$ aryl, and X includes one or more halogen elements selected from the group consisting of F, Cl, Br, and I, but may not be limited thereto.

HO—Ar—OH          [Chemical Formula 3]

According to an embodiment of the present disclosure, in the above Chemical Formula 3, Ar is aryl, and the aryl includes a member selected from the group consisting of phenyl, biphenyl, naphthalene, fluorene, anthracene, phenanthrene, pyrene, fluoranthen, chrysene, benzofluoranthen, perylene, quinoline, indenoanthracene, indenophenanthrene, hydroanthracene, dibenzothiophen, dibenzofuran, and combinations thereof, but may not be limited thereto.

According to an embodiment of the present disclosure, the aryl may be biphenyl, but may not be limited thereto.

The reaction may be carried out in the presence of a solvent selected from the group consisting of triethylamine, ethanol, methanol, isopropanol, hexane, acetone, tetrahydrofuran (THF), benzene, toluene, chloroform, dichloroethane, butanol, ethyl ether, propyl acetate, isopropyl acetate, butyl acetate, methylethylketone, methylbutylketone, and combinations thereof.

A third aspect of the present disclosure relates to a polycarbonate resin composition including the phosphorous compound, a polycarbonate resin, and a non-halogenated flame retardant.

According to an embodiment of the present disclosure, the non-halogenated flame retardant may include a phosphate flame retardant, but may not be limited thereto.

According to an embodiment of the present disclosure, the phosphate flame retardant may be a flame retardant selected from the group consisting of resorcinol bis(diphenyl phosphate) (RDP), bisphenol A bis(diphenyl phosphate) (BDP), triphenyl phosphate (TPP), aromatic phosphate, aromatic diphosphate, aromatic triphosphate, aromatic polyphosphate, trimethyl phosphate (TMP), triethyl phosphate (TEP), tricresyl phosphate (TCP), trixylenyl phosphate (TXP), and combinations thereof, but may not be limited thereto.

According to an embodiment of the present disclosure, the polycarbonate resin composition may contain 0.1 part by weight to 50 parts by weight of the phosphorous compound and 0.1 part by weight to 50 parts by weight of the non-halogenated flame retardant relative to 100 parts by weight of the polycarbonate resin, but may not be limited thereto.

According to an embodiment of the present disclosure, the polycarbonate resin may include a compound represented by the following Chemical Formula 4, but may not be limited thereto.

[Chemical Formula 4]

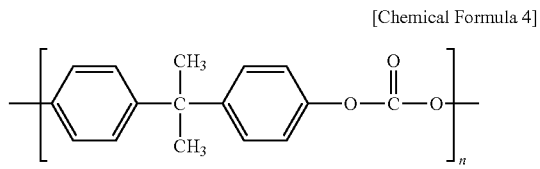

According to an embodiment of the present disclosure, in the above Chemical Formula 4, n may be 50 or more, but may not be limited thereto.

A fourth aspect of the present disclosure relates to a flame retardant molded article including the polycarbonate resin composition.

According to an embodiment of the present disclosure, the polycarbonate flame retardant resin composition may further include a material selected from the group consisting of a lubricant, an antioxidant, a photostabilizer, a chain extender, a catalyst, a release agent, a pigment, a dye, an anti-static agent, an antimicrobial agent, a processing aid, a metal deactivator, an anti-burning agent, an inorganic filler, glass fiber, an anti-friction agent, an antiwear agent, a coupling agent, and combinations thereof, but may not be limited thereto.

Hereinafter, the present disclosure will be described in more detail with reference to examples. The following examples are provided only for explanation, but do not intend to limit the scope of the present disclosure.

EXAMPLE 1 mol of 1,3-propanediol, 2 mol of trimethylamine, and 1.5 L of ether were put into a reactor and cooled at a temperature of from 0° C. to 5° C. A mixed solution of 1 mol of $POCl_3$ and 0.5 L of ether was added rapidly into the reactor while cooling was continuously performed. After all the solution was added into the reactor, the reactor was left to further react at room temperature for 5 hours. After the reaction, filtering was performed and the solvent ether were removed to obtain a solid represented by the following Compound 1.

[Compound 1]

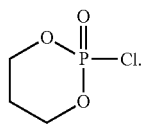

1 mol of the compound 1 and 200 ml of tetrahydrofuran (THF) were put into another reactor and cooled at a temperature of from 0° C. to 5° C. A mixed solution of 0.4 mol of biphenyl, 1 mol of triethylamine, and 200 ml of THF was added into the reactor with slow stirring. The reactor was left to further react at a temperature 60° C. for 8 hours. Then, filtering and washing was performed to obtain biphenyl bis(cyclic 1,3-propanediol phosphate) (BP-CPP).

Example 1

A specimen was prepared by compounding 92 wt % polycarbonate resin (LG Chemical Co., Ltd.), 4 wt % BP-CPP, and 4 wt % resorcinol bis(diphenyl phosphate) (RDP) at a temperature of from 220° C. to 250° C. using a HAAKE PolyDrive R600 (Thermo Electron Corporation).

Example 2

A specimen was prepared by compounding 92 wt % polycarbonate resin (LG Chemical Co., Ltd.), 3 wt % BP-CPP, and 5 wt % resorcinol bis(diphenyl phosphate) (RDP) at a temperature of from 220° C. to 250° C. using a HAAKE PolyDrive R600 (Thermo Electron Corporation).

Example 3

A specimen was prepared by compounding 92 wt % polycarbonate resin (LG Chemical Co., Ltd.), 2 wt % BP-CPP, and 6 wt % resorcinol bis(diphenyl phosphate) (RDP) at a temperature of from 220° C. to 250° C. using a HAAKE PolyDrive R600 (Thermo Electron Corporation).

Example 4

A specimen was prepared by compounding 90 wt % polycarbonate resin (LG Chemical Co., Ltd.), 4 wt % BP-CPP, and 6 wt % PX-200 at a temperature of from 220° C. to 250° C. using a HAAKE PolyDrive R600 (Thermo Electron Corporation).

Example 5

A specimen was prepared by compounding 90 wt % polycarbonate resin (LG Chemical Co., Ltd.) and 10 wt % BP-CPP at a temperature of from 220° C. to 250° C. using a HAAKE PolyDrive R600 (Thermo Electron Corporation).

Comparative Example 1

A specimen was prepared by compounding 100 wt % polycarbonate resin (LG Chemical Co., Ltd.) at a temperature of from 240° C. to 250° C. using a HAAKE PolyDrive R600 (Thermo Electron Corporation).

Comparative Example 2

A specimen was prepared by compounding 92 wt % polycarbonate resin (LG Chemical Co., Ltd.) and 8 wt % resorcinol bis(diphenyl phosphate) (RDP) at a temperature of from 220° C. to 250° C. using a HAAKE PolyDrive R600 (Thermo Electron Corporation).

Comparative Example 3

A specimen was prepared by compounding 90 wt % polycarbonate resin (LG Chemical Co., Ltd.) and 10 wt % resorcinol bis(diphenyl phosphate) (RDP) at a temperature of from 220° C. to 250° C. using a HAAKE PolyDrive R600 (Thermo Electron Corporation).

Comparative Example 4

A specimen was prepared by compounding 90 wt % polycarbonate resin (LG Chemical Co., Ltd.) and 10 wt % PX-200 at a temperature of from 220° C. to 250° C. using a HAAKE PolyDrive R600 (Thermo Electron Corporation).

Test Example

The properties of BP-CPP prepared in Example were checked, and the result thereof was as shown in FIG. 1.

FIG. 1 is a NMR (nuclear magnetic resonance) graph of BP-CPP according to an example of the present disclosure.

The specimens prepared in Examples 1 to 5 and Comparative Examples 1 to 4 were each measured for flame retardancy at a thickness of ⅛" according to UL-94 VB flame retardancy standards.

The specimens prepared in Examples 1 to 3, Example 5, and Comparative Examples 1 to 3 were each measured for tensile strength according to ASTM D638 standards.

The measured flame retardancy results and the measured tensile strength results were as shown in Table 1.

TABLE 1

|  | Example | | | | | Comparative Example | | | |
| --- | --- | --- | --- | --- | --- | --- | --- | --- | --- |
|  | 1 | 2 | 3 | 4 | 5 | 1 | 2 | 3 | 4 |
| Polycarbonate | 92 | 92 | 92 | 90 | 90 | 100 | 92 | 90 | 90 |
| BP-CPP | 4 | 3 | 2 | 4 | 10 | 0 | 0 | 0 | 0 |
| RDP | 4 | 5 | 6 | 0 | 0 | 0 | 8 | 10 | 0 |
| PX-200 | 0 | 0 | 0 | 6 | 0 | 0 | 0 | 0 | 10 |
| UL-94 flame retardancy (⅛") | V-1 | V-1 | V-0 | V-0 | V-2 | V-2 | V-2 | V-0 | V-0 |
| Tensile strength (Mpa) | 69 | 68 | 67 | — | 65 | 72 | 66 | 64 | — |

According to the results shown in Table 1, it was confirmed that the polycarbonate resin containing BP-CPP was excellent in flame retardancy and tensile strength.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A phosphorus compound represented by the following Chemical Formula 1:

[Chemical Formula 1]

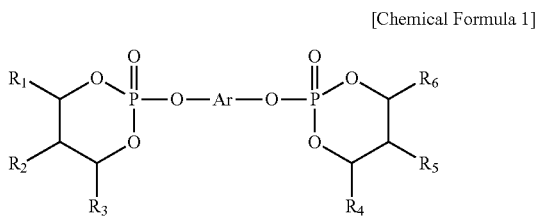

(wherein in the above Chemical Formula 1,

Ar is aryl and $R_1$, $R_2$, $R_3$, $R_4$, $R_5$, and $R_6$ are each independently H, substitutable linear or branched $C_1$-$C_{20}$ alkyl and substitutable $C_6$-$C_{20}$ aryl, the aryl includes a member selected from the group consisting of phenyl, biphenyl, naphthalene, fluorene, anthracene, phenanthrene, pyrene, fluoranthen, chrysene, benzofluoranthen, perylene, quinoline, indenoanthracene, indenophenanthrene, hydroanthracene, dibenzothiophen, dibenzofuran, and combinations thereof, and the substitution is substituted with $C_1$-$C_6$ alkyl or $C_6$-$C_{20}$ aryl).

2. The phosphorus compound of claim 1, wherein $R_1$, $R_2$, $R_3$, $R_4$, $R_5$, and $R_6$ are each independently H or substitutable linear or branched $C_1$-$C_{20}$ alkyl, and the substitution is substituted with $C_1$-$C_6$ alkyl or $C_6$-$C_{20}$ aryl.

3. The phosphorus compound of claim 1, wherein the phosphorous compound includes the following compound:

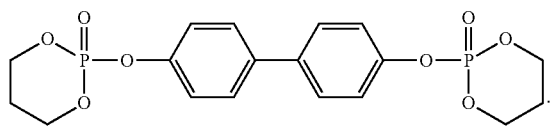

4. A synthesis method of a phosphorous compound of claim 1, comprising:

reacting a compound represented by the following Chemical Formula 2 with a compound represented by the following Chemical Formula 3:

[Chemical Formula 2]

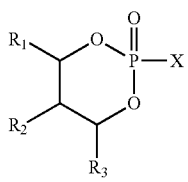

(wherein in the above Chemical Formula 2, $R_1$, $R_2$, and $R_3$ are each independently H, substitutable linear or branched $C_1$-$C_{20}$ alkyl and substitutable $C_6$-$C_{20}$ aryl, the substitution is substituted with $C_1$-$C_6$ alkyl or $C_6$-$C_{20}$ aryl, and X includes one or more halogen elements selected from the group consisting of F, Cl, Br, and I); and HO—Ar—OH  [Chemical Formula 3]

(wherein in the above Chemical Formula 3,

Ar is aryl, and the aryl includes a member selected from the group consisting of phenyl, biphenyl, naphthalene, fluorene, anthracene, phenanthrene, pyrene, fluoranthen, chrysene, benzofluoranthen, perylene, quinoline, indenoanthracene, indenophenanthrene, hydroanthracene, dibenzothiophen, dibenzofuran, and combinations thereof).

5. The synthesis method of a phosphorous compound of claim 4, wherein the aryl is biphenyl.

6. A polycarbonate resin composition, comprising:

a phosphorous compound of claim 1;

a polycarbonate resin; and a non-halogenated flame retardant.

7. The polycarbonate resin composition of claim 6, wherein the non-halogenated flame retardant includes a phosphate flame retardant.

8. The polycarbonate resin composition of claim 7, wherein the phosphate flame retardant is a flame retardant selected from the group consisting of resorcinol bis (diphenyl phosphate) (RDP), bisphenol A bis(diphenyl phosphate) (BDP), triphenyl phosphate (TPP), aromatic phosphate, aromatic diphosphate, aromatic triphosphate, aromatic polyphosphate, trimethyl phosphate (TMP), triethyl phosphate (TEP), tricresyl phosphate (TCP), trixylenyl phosphate (TXP), and combinations thereof.

9. The polycarbonate resin composition of claim 6, wherein the polycarbonate resin composition contains 0.1 part by weight to 50 parts by weight of the phosphorous compound and 0.1 part by weight to 50 parts by weight of the non-halogenated flame retardant relative to 100 parts by weight of the polycarbonate resin.

10. The polycarbonate resin composition of claim 6, wherein the polycarbonate resin includes a compound represented by the following Chemical Formula 4:

[Chemical Formula 4]

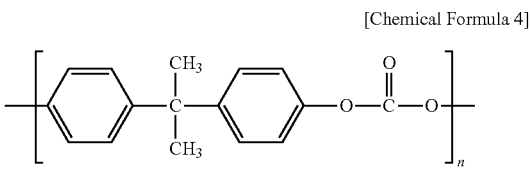

(wherein in the above Chemical Formula 4, n is 50 or more).

11. The polycarbonate resin composition of claim 6, wherein the polycarbonate flame retardant resin composition further includes a material selected from the group consisting of a lubricant, an antioxidant, a photostabilizer, a chain extender, a catalyst, a release agent, a pigment, a dye, an anti-static agent, an antimicrobial agent, a processing aid, a metal deactivator, an antiburning agent, an inorganic filler, glass fiber, an antifriction agent, an antiwear agent, a coupling agent, and combinations thereof.

* * * * *